United States Patent [19]

Min et al.

[11] Patent Number: 4,932,941
[45] Date of Patent: Jun. 12, 1990

[54] NON-REUSABLE DISPOSABLE SYRINGE

[76] Inventors: Kyung M. Min, 42-42 Colden St., Apt. C9, Flushing, N.Y. 11355; Hahn Min, 344 Glenwood Ave., Leonia, N.J. 07605

[21] Appl. No.: 174,707

[22] Filed: Mar. 29, 1988

[30] Foreign Application Priority Data

Mar. 14, 1988 [KR] Rep. of Korea .......................... 3432

[51] Int. Cl.⁵ .............................................. A61M 5/00
[52] U.S. Cl. ..................................... 604/110; 604/218
[58] Field of Search ............... 604/110, 218, 220, 221, 604/222, 228

[56] References Cited

U.S. PATENT DOCUMENTS 4,233,975 11/1980 Yerman .............................. 604/110
4,391,272 7/1983 Staempfli ........................... 604/110

FOREIGN PATENT DOCUMENTS 2184657 7/1987 United Kingdom ............... 604/110

Primary Examiner—John D. Yasko
Attorney, Agent, or Firm—Peter L. Berger

[57] ABSTRACT

There is disclosed a disposable and non-reusable syringe which has its piston locked in its forward dispense position after it is used, and the plunger is pulled out from the piston if the plunger is sought to be retracted from the syringe. The non-reusable syringe is so constructed to prevent the piston from reengaging with the plunger, even if the plunger is retracted and sought to be reinserted.

13 Claims, 3 Drawing Sheets

NON-REUSABLE DISPOSABLE SYRINGE

BACKGROUND OF THE INVENTION

This application relates to a disposable syringe, and more particularly, to a disposable syringe which is incapable of being reused.

Disposable syringes have long been part of the medical community. The syringes are used to dispense a pre-measured amount of medicine, and such syringes are adapted to be thrown away after use. The commercial significance of disposable syringes has long been a factor in their utilization, but more recently, with the widespread concern about AIDS and other diseases transmitted through shared intravenous needles, there has been heightened concern to ensure that disposable syringes are, indeed, not reused.

There have been numerous instances of disposable syringes being reused, either because of sloppy housekeeping practices in hospitals or medical offices or because maintenance companies responsible to dispose hospital waste allow pilferage to occur in which these disposable syringes are recirculated within the medical community. This has led to significant concern about the integrity of utilizing syringes which were supposed to have been destroyed after a single use, and for some reason, find their way back into use.

An object of this invention is to provide a disposable syringe which is unable to be reused.

Another object of this invention is to provide such a disposable syringe which will share many common characteristics with conventional syringes, yet the ability to reuse the syringe will be prevented.

Yet another object of this invention is to provide such a disposable and non-reusable syringe which is made of plastic materials and may be used with premeasured doses of medicine.

Other objects, advantages and features of this invention will become more apparent from the following description.

SUMMARY OF THE INVENTION

In accordance with the principles of this invention, the above objects are accomplished by providing a disposable syringe which has its piston locked in its forward dispense position after it is used, and the plunger is pulled out from the piston if the plunger is retracted with sufficient force from the syringe.

Additionally, the non-reusable syringe is so constructed to prevent the piston from reengaging with the plunger, even if the plunger is retracted and sought to be reinserted. This ensures that the piston/plunger combination can not be retracted to allow the syringe to be reused.

DETAILED DESCRIPTION

Figure 1:
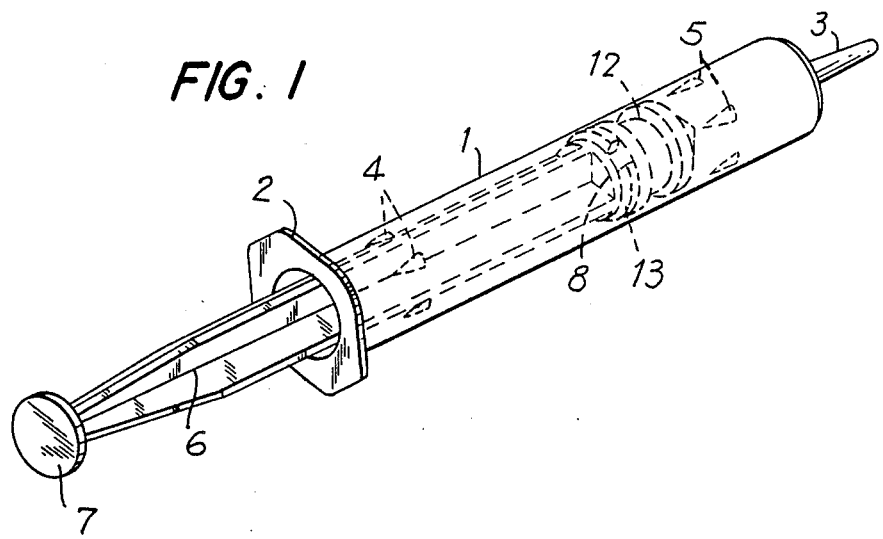
FIG. 1 is a perspective view of the novel syringe of this invention showing the plunger rod and piston in phantom.
Figure 2:
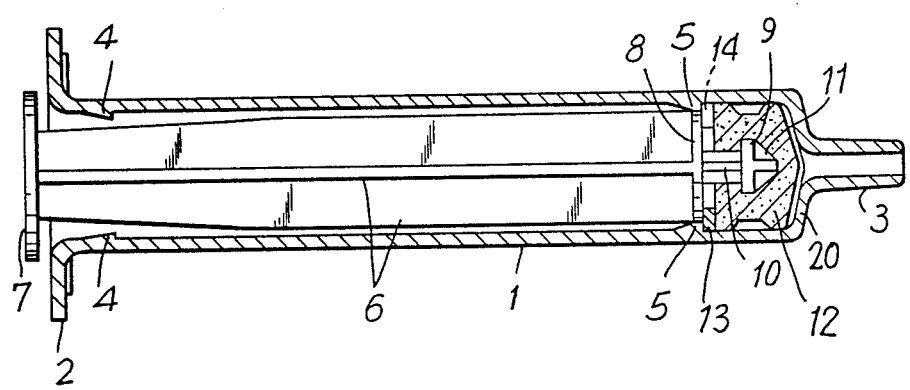
FIG. 2 is a sectional view taken along the length of the syringe.
Figure 3A:
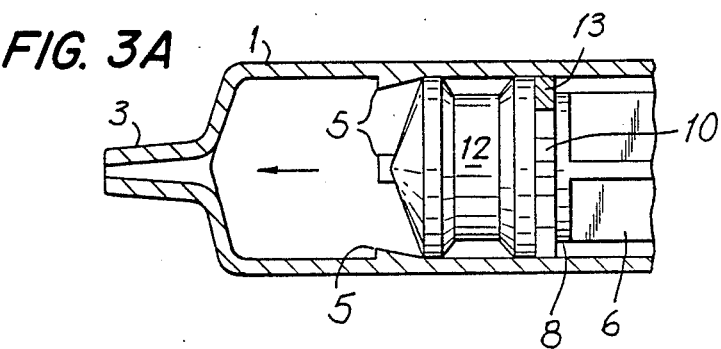
FIGS. 3a–3d are a series of partial cross-sectional views showing the forward movement of the piston and its retention in the front end of the cylinder.
Figure 3B:
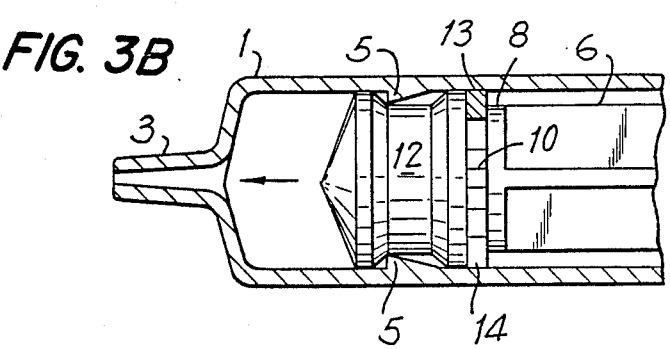
Figure 3C:
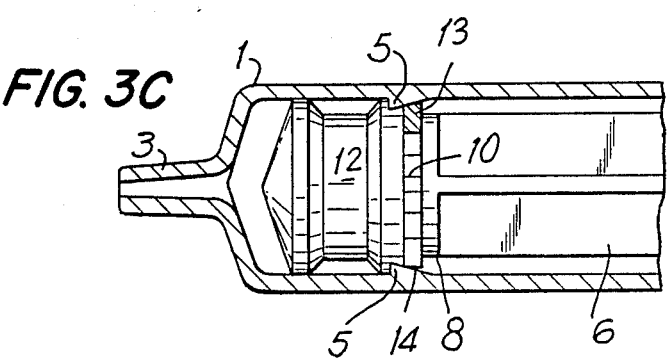
Figure 3D:
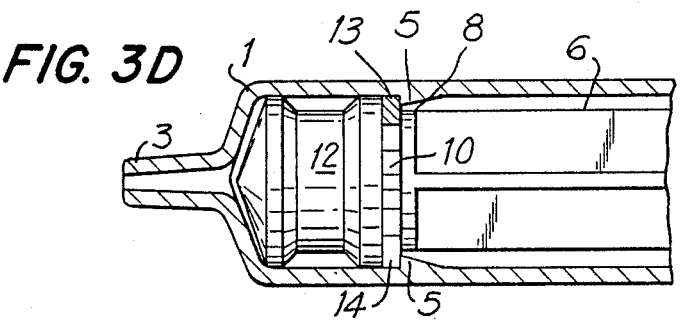

Referring to FIGS. 1 and 2, there is shown the syringe of this invention which comprises a cylinder 1 having a front end 20 and in which there is fitted and moves a plunger rod 6 having its front connected to a piston 12. The piston 12 and cylinder 1 are sealed allowing the piston to dispense medicine as it is moved toward the front end 20 of the cylinder. The cylinder 1 terminates in a finger rest surface 2 at its rear end and plunger rod 6 terminates in a thumb tab 7 at its rear end.

A predetermined amount of medicine (not shown) is contained in the syringe, and the rod 6 moves forward as pressure is placed on thumb tab 7 to bring it toward finger rest 2. Medicine is ejected from nozzle 3 connected to front end 20 of the cylinder. To this point, there has been described a conventional syringe operation.

The front end of plunger rod 6 terminates in a contact plate 8 which is fixedly attached to one end of a connecting rod 10. The other end of connecting rod 10 attached to piston grip member 9 which seats within a socket 11 within piston 12 to hold piston 12 to the plunger rod. Plunger 6, contact plate 8, connecting rod 10 and piston grip member 9 may be made as a single one piece molded plastic member.

In accordance with the principles of the present invention, there is provided a lock ring 13 surrounding connecting rod 10. The lock ring 13 is located in front of contact plate 8 (FIG. 5) and bears against the rear portion of piston 12. Inwardly directed annular ridge 4 is formed as an annular member projecting from an inner wall of cylinder 1 just beyond the entrance to the cylinder 1.

A set of inwardly directed tapered notches 5 projecting from the inner peripheral wall of the front portion of cylinder 1 are also provided. As seen in FIGS. 3a–3d, piston 12 moves forward and passes notches 5. As the piston 12 reaches the forward position to dispense the medicine out through nozzle 3, lock ring 13 which compresses as it passes notches 5, snaps open and becomes seated against the notches, thereby preventing piston 12 from being retracted from cylinder 1. If the user attempts to remove piston 12 by retracting plunger rod 6 from the cylinder, rod extension 10 will be pulled from socket 11 in piston 12 thereby allowing the plunger rod to be removed from the cylinder without the piston 12. In this manner, piston 12 is locked in its forward dispense position and can not be removed from cylinder 1. The syringe of this invention is not capable of being reused. There is no way to retract piston 12 without destroying the syringe, and such effort renders the present syringe not only disposable but also non-reusable.

Figure 4A:
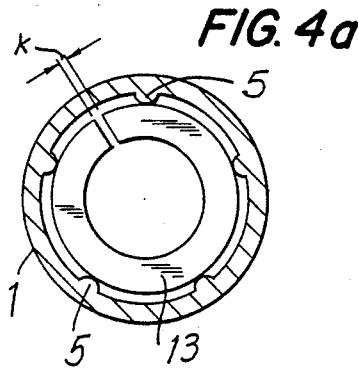
FIGS. 4a and 4b are two views showing a locking ring used with the syringe of this invention, with FIG. 4a showing the locking ring before it is expanded and FIG. 4b showing it expanded and blocking the retraction of the piston from the cylinder.
Figure 4B:
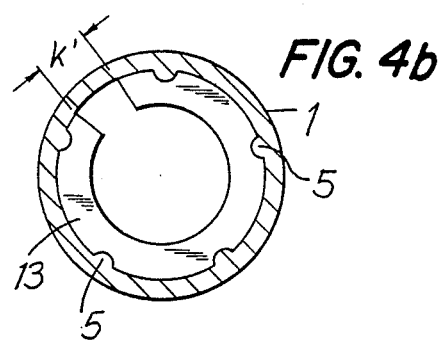
Figure 5:
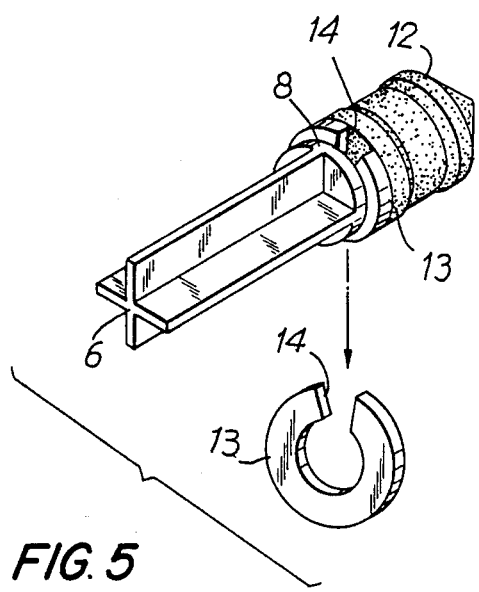
FIG. 5 is a partial perspective view showing the locking ring, piston and the plunger.

FIGS. 4 and 5 more clearly illustrate the operation of lock ring 13 which terminates in spaced apart opposite bearing surfaces 14. A space k' is identified when the lock ring is sprung open, and a space k is illustrated when the lock ring is compressed. The lock ring is prebiased open, and it is compressed as illustrated in FIG. 4a as the lock ring passes through the cylinder 1 and over notches 5 as shown in FIGS. 3a-3d. There are provided at least five spaced-apart notches 5 to ensure that none of the notches gets caught in space k which would interfere with the proper operation of the lock ring. The radial spacing of notches 5 around the inner periphery of cylinder 1 ensures that the lock ring will be moved to its substantially closed position as it passes from FIGS. 3c to 3d, and in position 3d, the lock ring 13 will snap to its open position, thereby locking it in beyond notches 5.

Figure 6:
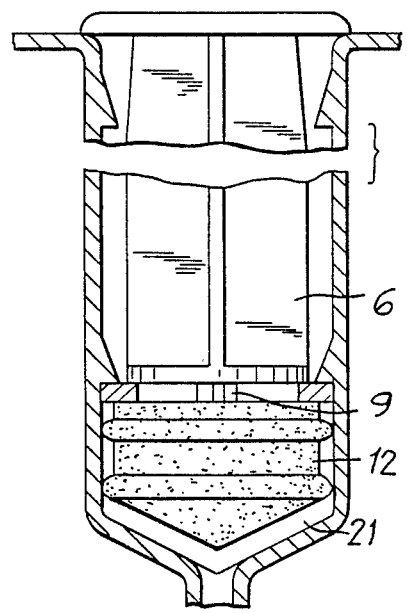
FIG. 6 is a sectional view partially broken showing another aspect of this invention in which the plunger is prevented from connecting with the piston after use.

FIG. 6 illustrates yet another aspect of this invention in which the length of the plunger rod 6 is illustrated to be slightly less than the length of cylinder 1, so that when the piston is moved to its forward dispense position, a gap 21 exists between the piston and front of the cylinder. This gap prevents piston grip member 9 from being reinserted into piston 12 if the rod and piston grip member is removed therefrom. A stop is formed of tab 7 and finger rest 2 prevents the piston grip member 9 from being pushed fully into the piston 12 because of the slightly longer length of cylinder 1 than the combination of plunger rod 6 and piston grip member 9. The user will not be able to reinsert the plunger 6 into the piston 12 because of the small gap 21 between the piston 12 and the front end of cylinder 1.

An inwardly directed annular ridge 4 is provided on the inner wall on the rear portion of cylinder 1 to prevent tampering since it prevents removal of piston rod 6 because locking ring 13 bears against ridge 4 if the piston rod is sought to be removed from the cylinder. This prevents anyone from having access to remove the elements of the blocking mechanism, especially lock ring 13. Additionally, ridge 4 limits the radical play of plunger rod 6 to further ensure effective operation of the syringe. In its intended form, the syringe will be provided with the piston rod 6 initially located between ridge 4 and nothces 5. Ridge 4 also tends to prevent accidental spillage of fluid while the cylinder is being loaded.

Ridge 4 and notches 5 are provided with smooth tapered surfaces to facilitate a smooth piston movement with minimum friction. As the locking ring snaps past ridge 4, there will be an audible and visible indication thereof, and this also will occur when the locking ring proceeds to the locking position beyond notches 5.

Locking ring 13 also may be colored so that a visible check of its location can easily be made by the user.

The present invention is illustrated with one preferred embodiment. Essentially, the invention teaches the provision not only of a disposable syringe, but the provision of a disposable syringe which is rendered useless after it is used, so as to prevent its being reused. In the preferred embodiment shown in this invention, this is achieved by ensuring that the piston is retained in its forward dispensed position locked behind notches 5 through locking ring 13. This prevents the piston from being retracted. Other apparatus may be designed ensuring the non-functioning of the piston after it is used, and it is intended that the teaching of this invention be accorded its appropriate scope as identified in the pending claims.

We claim:

1. A disposable and non-reusable syringe comprising:
a cylinder having a front end and a rear end,
a plunger rod movable within the cylinder, said plunger rod terminating in a piston,
said piston moving forwardly in said cylinder to a forward dispense position,
blocking means to prevent said piston from being retracted from said forward dispensing position after it is moved, said blocking means comprising a locking ring surrounding said plunger rod and being movable therewith, said locking ring being locked into a fixed position to maintain said piston in said forward dispensing position.

2. A disposable and non-reusable syringe as claimed in claim 1, wherein said blocking means further comprises projection means projecting from the inner wall of said cylinder and located in the path of movement of said locking ring, said locking ring being snapped into position beyond said projection means to prevent retraction of said piston.

3. A disposable and non-reusable syringe as claimed in claim 1, wherein said plunger rod is attached to said piston, said plunger rod being separated from said piston if said plunger rod is retracted from said cylinder when said piston is locked in its forward dispensing position.

4. A disposable and non-reusable syringe as claimed in claim 1, wherein said locking ring comprises a prebiased open ring having a space formed between its free ends, said ring passing over said projection means as said piston rod is pushed forwardly in said cylinder, said space narrowing as said locking ring passes over said projection means, said locking ring springing open after it passes said projection means to be locked behind said projection means preventing said piston from being retracted from said cylinder.

5. A disposable and non-reusable syringe as claimed in claim 1, wherein said projection means comprises radially projecting members projecting inwardly from the walls of said cylinder.

6. A disposable and non-reusable syringe as claimed in claim 5, wherein said projection means comprises a plurality of individual spaced apart projection members.

7. A disposable and non-reusable syringe as claimed in claim 7, wherein there are at least five projection members.

8. A disposable and non-reusable syringe as claimed in claim 7, wherein said projection members are tapered inwardly from said wall toward the front end of said cylinder.

9. A disposable and non-reusable syringe as claimed in claim 1, further comprising an additional projection means located in the rear portion of said cylinder, said additional projection means projecting inwardly from the walls of said cylinder to capture said plunger rod and locking ring between said projection means and said additional projection means before said medicine is dispensed by said syringe.

10. A disposable and non-reusable syringe as claimed in claim 1, wherein rear end of said plunger rod terminates in a thumb tab, said rear end of said cylinder terminating in a finger resting plate, wherein the length of said rod and piston is slightly less than the distance between said finger plate and the forward end of the cylinder defining a gap between the piston and forward end of the cylinder when the piston is in its forward dispensing position.

11. A disposable and non-reusable syringe as claimed in claim 1, wherein said locking ring is colored to be visible as it moves in the syringe.

12. A disposable and non-reusable syringe as claimed in claim 10, wherein said additional projection means comprises an annular ridge projecting inwardly from the wall of the cylinder.

13. A disposable and non-reusable syringe as claimed in claim 12, wherein said annular ridge limits the radial play of said plunger rod.

* * * * *